United States Patent [19]

Hatton et al.

[11] 4,181,839
[45] Jan. 1, 1980

[54] MULTI-VIEW COLLIMATOR

[75] Inventors: John Hatton, Northbrook; Raymond P. Grenier, Mundelein, both of Ill.

[73] Assignee: Cardiac Medical Sciences Corp., Northbrook, Ill.

[21] Appl. No.: 827,947

[22] Filed: Aug. 26, 1977

[51] Int. Cl.² .................. G03B 41/16; A61B 6/00
[52] U.S. Cl. ................ 250/505; 250/313; 250/363 S
[58] Field of Search .......... 250/313, 314, 505, 363 S, 250/366

[56] References Cited

U.S. PATENT DOCUMENTS

| | | |
|---|---|---|
| 2,730,566 | 1/1956 | Bartow et al. ............ 250/313 |
| 2,731,713 | 1/1956 | Schaefer . |
| 3,011,057 | 11/1961 | Anger . |
| 3,143,738 | 8/1964 | Bigelow . |
| 3,197,638 | 7/1965 | Sinclair . |
| 3,412,246 | 11/1968 | Horwitz . |
| 3,509,339 | 4/1970 | Doehner . |
| 3,509,341 | 4/1970 | Hindel et al. . |
| 3,573,458 | 4/1971 | Anger . |
| 3,612,865 | 10/1971 | Walker . |
| 3,683,180 | 8/1972 | Martone . |
| 3,777,148 | 12/1973 | Miraldi . |
| 3,792,273 | 2/1974 | Bergstedt . |
| 3,793,520 | 2/1974 | Grenier . |
| 3,814,938 | 6/1974 | Martone . |
| 3,852,603 | 12/1974 | Muehllehner . |
| 3,912,000 | 11/1975 | Muehllehner . |
| 3,935,462 | 1/1976 | de Luca . |
| 3,936,639 | 2/1976 | Barrett . |
| 3,988,585 | 10/1976 | O'Neill ................ 250/363 S |
| 4,001,591 | 1/1977 | Inbar .................... 250/366 |
| 4,079,259 | 3/1978 | Blum .................... 250/505 |

OTHER PUBLICATIONS

Hine, G. J., *Instrumentation in Nuclear Medicine*, Academic Press, New York, 1967, pp. 518–519.
Okano et al., "Three-Dimensional Scanner Using a Coaxial Ge(Li) Detector," *First World Congress of Nuclear Medicine*, Sep. 30–Oct. 4 1974, Tokyo, p. 1278.

*Primary Examiner*—Alfred E. Smith
*Assistant Examiner*—T. N. Grigsby
*Attorney, Agent, or Firm*—Fitch, Even & Tabin

[57] ABSTRACT

A nonfocusing collimator provides two separate views of a portion of a body, such as an organ, simultaneously by employing a first and second plurality of parallel channels. The collimator may comprise a plurality of sections, each producing a first and second view, and being capable of producing a plurality of composite views.

55 Claims, 6 Drawing Figures

MULTI-VIEW COLLIMATOR

The present invention relates to radiation-detecting cameras, and more particularly to such cameras and collimating devices used in imaging distributions of radioactive material in organs of the human body, especially moving organs such as the heart.

Images can be created of organs of the body by introducing into the blood a variety of radiopharmaceuticals such as labelled human serum albumin or red blood cells. The radioactive material distributes itself in the organ and causes radioactive emissions such as gamma emissions. These emissions are typically detected by radiation-detecting cameras such as the Anger or Fleuroscope scintillation cameras through a collimator and are displayed on a cathode ray tube (CRT) or other display equipment. An example of such a gamma radiating system is disclosed in U.S. Pat. No. 3,011,057 to Hal O. Anger. The images produced are generally two-dimensional representations of three-dimensional distributions. Thus, it is often difficult to determine the actual exact location and extent of the particular tissue under investigation, and this problem is made more complicated in the case of a moving organ like the beating heart.

Prior proposals to provide this information include the use of collimators that focus on emissions from a point or a series of points and move back and forth and up and down until the entire organ or region of interest has been scanned. This is of course time-consuming and problems occur due to the delay. Such prior method is especially ill-suited to the imaging of the heart because it will generally be in a different condition at the later time. Other techniques include rotating a nonnormal viewing collimator so that successive views are obtained while the collimator rotates, and moving the camera to obtain successive views. Both methods suffer, since again there is a delay between successive views, and it would be extremely difficult to obtain two useful views at separate angles from the moving organ while the organ is in the same position or condition. Moreover, not only may the condition of the organ vary with its normal periodic movement, but also variations may occur with the lapse of time after some controlled stimulation of the patient. And such variations may well grossly impair the diagnostic value of such prior imaging techniques for use in cardiac examinations and the like.

It is an object of the present invention to provide a multi-view collimator and an improved radiation-detecting camera system obviating, for practical purposes, the above-mentioned limitations heretofore present.

Other objects and advantages of the invention are more particularly set forth in the following detailed description, and in the accompanying drawings, of which:

The present invention is used in providing multiple simultaneous imaging of a portion of a body, such as an organ, with a stationary radiation-detecting camera, or cameras, such as the so-called Anger-type camera. Although the invention is herein shown and described with reference to an organ, it should be understood that it is also applicable to any portion or region of the body which may be of interest. Radiation from the organ passes through apertures or channels of a nonfocused collimator and strikes a radiation-detecting material such as sodium iodide or cadmium telluride. In one embodiment of the present invention, the collimator is comprised of a body of substantially radiation-impervious material which defines a first plurality of channels with each of the channels having an axis. The axis of each channel defines an angular direction of acceptance of radioactive emissions from the organ or other portion of the body. The axes of the first plurality of channels are substantially in parallel with each other. The axes of the second plurality of channels define another angular direction of acceptance of radioactive emissions from the organ and at least partially intersect the same portion of the body as the axes of the first plurality of channels, thus producing a second view of a portion of the body, such as the organ or organs of interest.

More particularly, in a preferred embodiment of the present invention, the collimator comprises a disk comprised of a plurality of parallel adjacent sections each of which sections views a separate portion or "slice" of the organ. Each section defines a first and second plurality of channels, each of which channels has an axis. The axes of the first plurality of channels are parallel and co-planar and also parallel with the axes of the other first pluralities of channels of each section thereby producing a first view of the organ. Similarly, the axes of the second plurality of channels are parallel and co-planar and are also parallel with the other axes of the second pluralities of channels of each section thereby producing a second view of the organ.

A second embodiment of the present invention provides more than two simultaneous views of the organ and includes a collimator comprised of at least two adjacent sections wherein each of the sections views a separate portion or "slice" of the organ. Each of these sections is comprised of substantially radiation impervious material and define a first and second plurality of channels as in the first embodiment described. Thus, each section produces a first and second view of its associated slice of the organ. Therefore, the first section of the collimator produces a first and second view of a first slice of the organ and the second section produces a first and second view of a second slice of the organ.

In a preferred construction in accordance with this embodiment, the collimator comprises at least four adjacent sections. The third section produces a first and second view of a third slice of the organ, and the fourth section produces a first and second view of a fourth slice of the organ. The axes of the first plurality of channels of the first and third sections of the collimator are substantially in parallel with each other and thus produce a first composite view. The first composite view is a view of the first and third slices of the organ and is comprised of the first views produced by the first and third sections. Similarly, the axes of the second plurality of channels of the first and third sections are substantially in parallel with each other and thus produce a second composite view. The second composite view is a second view of the first and third slices of the organ and is comprised of the second views produced by the first and third sections. Similarly the axes of the first plurality of channels of the second and fourth sections are substantially in parallel with each other and produce a third composite view which is a view of the second and fourth slices of the organ, and the axes of the second plurality of channels of the second and fourth sections are substantially in parallel with each other and produce a fourth composite view which is a second view of the second and fourth slices of the organ.

The group of four sections may be repeated so that the collimator is comprised of a first plurality of sections, which is comprised of the first and third sections of each group and a second plurality of sections, which is comprised of the second and fourth sections of each group. The first plurality of sections produces the first and second composite views of the organ and the second plurality of sections produces the third and fourth composite views of the organ. The greater the number of sections and the thinner each section is, the greater the resolution will be of each composite view. Typically, there will be a minimum of about 64 sections to achieve good resolution in most diagnostic applications.

The collimator sections are grouped in assemblies of two or more, and preferably between two and five, but a greater number may be used in some instances. Each section has, usually, but not necessarily, two angles so that four to ten (or more) angles are contained in each group. Additionally, in practice, another section will generally be used for a normal frontal view (i.e., along a frontal axis), such section having a plurality of channels all parallel to the frontal axis. Thus, the frontal view section adds an additional section to each group, if used. The groups are then repeated until the collimator covers the detector surface.

Means are provided for sorting each event of detected radiation according to the coordinates assigned to that event by the radiation-detecting camera. The coordinates of each event determine the particular view to which the event pertains. In general, a data processing system may be used for sorting the events using, for example, a "look-up-table" technique to separate an event in a specific matrix position and assign the event to a particular composite view. The matrix given below illustrates this technique for de-multiplexing a six composite view collimator.

| | i = 1 | 2 | 3 | 4 | 5 | 6 | 7 | 8 | 9 | 10 | 11 | 12 |
|---|---|---|---|---|---|---|---|---|---|---|---|---|
| A j = 1 | ←—View | 1 | —→ | | | | ←—View | 2 | —→ | | | |
| 2 | | 3 | | | | | | 4 | | | | |
| 3 | | 5 | | | | | | 6 | | | | |
| 4 | ←—View | 1 | —→ | | | | ←—View | 2 | —→ | | | |
| 5 | | 3 | | | | | | 4 | | | | |
| 6 | | 5 | | | | | | 6 | | | | |
| 7 | ←—View | 1 | —→ | | | | ←—View | 2 | —→ | | | |
| 8 | | 3 | | | | | | 4 | | | | |
| 9 | | 5 | | | | | | 6 | | | | |
| 10 | ←—View | 1 | —→ | | | | ←—View | 2 | —→ | | | |
| 11 | | 3 | | | | | | 4 | | | | |

Thus, if an event occurs in $A_{ij}$ with i equal to any number 1 to 6 and j equal to 1, 4, 7, 10, etc., then the result is assigned to row j of composite view 1; $A_{ij}$ with i=7 to 12, j=1, 4, 7, 10, etc., the result is assigned to row j of composite view 2. If j=2, 5, 8, 11, etc., then composite views 3 and 4 result. If j=3, 6, 9, etc., then composite views 5 and 6 result. Various methods, such as interpolation or the use of mathematical functions, can be used as necessary to estimate the statistics between rows of the composite views.

Figures 1, 2, 3:
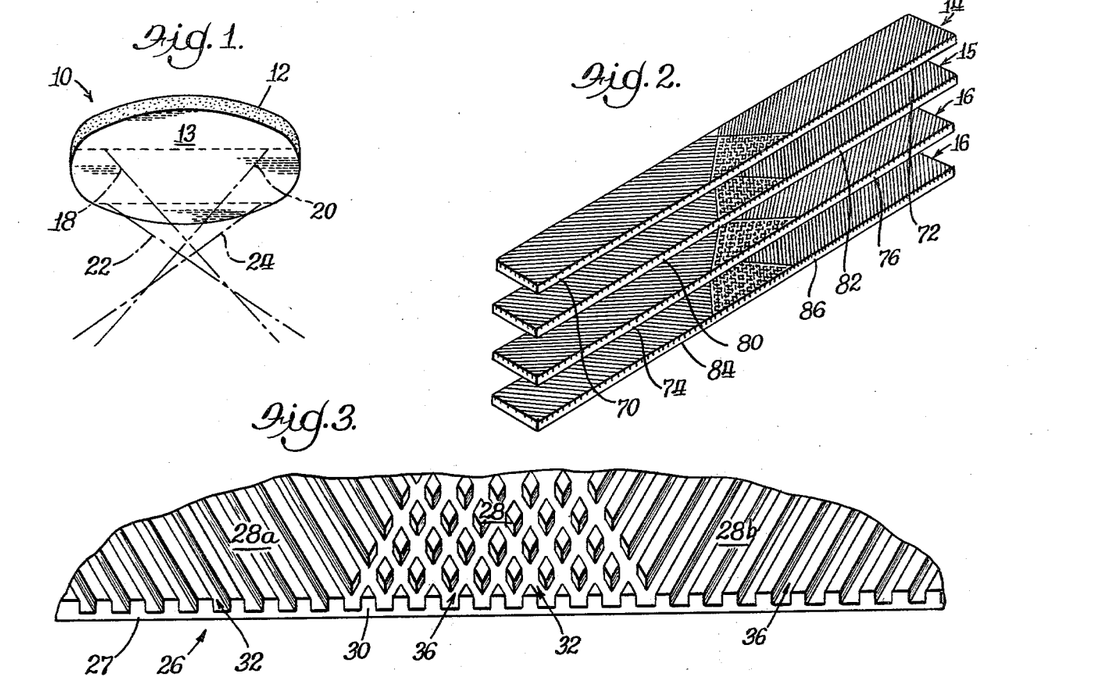
FIG. 1 is a perspective view of a collimator in accordance with an embodiment of the present invention.
FIG. 2 is an exploded perspective view of a group of sections of the collimator.
FIG. 3 is a perspective view of one partially broken-away section of the collimator.

More particularly, a preferred construction of the second embodiment of the invention is illustrated in FIG. 1. Collimator 10 comprises disk 12 having a planar front face 13 which is composed of substantially radiation-impervious material such as lead. Disk 12 comprises a first and second plurality of parallel adjacent sections, each of which sections views a separate portion or slice of the organ. For clarity, not all sections are emphasized in FIG. 1. The individual sections from the first and second plurality of sections are in alternating adjacent positions in the disk 12.

FIG. 2 illustrates an exploded view of four such sections 14-17. Each section defines a first and second plurality of channels. Thus section 14 defines a first plurality of channels 70 and a second plurality of channels 72. Similarly, section 15 defines a first and second plurality of channels 80 and 82 respectively. Each channel has an axis which defines the direction of travel of a radioactive emission passing through the channel of the collimator. The axes of each first plurality of channels are parallel and coplanar. The axes of each second plurality of channels are parallel and are also coplanar with the first plurality of channels. In the first plurality of sections, represented by sections 14 and 16, the axes of the first plurality of channels for cardiac imaging are preferably oriented at an angle of 45 degrees with respect to a frontal plane parallel to face 13 of disk 12 with the axes of the second plurality of channels preferably oriented at an angle of 135 degrees, as illustrated by a pair of axis lines 18 and 20 of a section from the first plurality of sections in FIG. 1. FIG. 1 also illustrates the orientation of a pair of axis lines 22 and 24 of a section from the second plurality of sections. Again, for cardiac imaging, the axes of the first plurality of channels of the second plurality of sections represented by sections 15 and 17, are preferably oriented at an angle of 60 degrees with respect to the frontal plane parallel to face 13 of disk 12 and the axes of the second plurality of channels of the second plurality of sections are preferably oriented at 120 degrees.

With reference to FIG. 3, a broken-away portion of a collimator section 26 having a base 27 which carries a plurality of septa 28, and planar front face 30, is shown. Base 27 and septa 28a define a first plurality of channels 32 which are parallel, equally spaced, and at an angular orientation of 45 degrees with respect to front face 30 which is part of face 13 of disk 12. Similarly, base 27 and septa 28b define a second plurality of channels 36 which are parallel, equally spaced, and have an angular and clockwise orientation of 135 degrees with respect to front face 30. The first plurality of channels 32 are substantially on one side of section 26 with the second plurality of channels 36 substantially on the other side, but due to the angular orientation of the channels, the channels in the center portion of section 26 intersect, as shown. The first and second pluralities of channels may, however, each be on both sides with substantially all the channels intersecting. Each channel has a square cross-sectional area in this embodiment, but may be round, hexagonal, or any desired shape to improve transmission characteristics. The channel itself may be uniform or tapered, such as from the front (directed to patient) or from the rear (directed to radiation-detecting material).

A specific construction of the first embodiment may comprise a plurality of sections such as section 26 which are stacked adjacent to each other until the entire radiation-detecting material is covered. Thus, the collimator would have a first plurality of channels 32 comprised of the first plurality of channels from each section thereby producing a first view of the heart from an angle of 45 degrees and would also have a second plurality of channels 36 producing a second view of the heart from an angle of 135 degrees. An alternative first embodiment may comprise a plurality of sections such as section 15 which could produce a first and second view of the heart from angles of 60 and 120 degrees, respectively. The sections may be constructed to produce views from practically any desired angles. A collimator employing the first embodiment of the invention will, in order to obtain both views, require only minimal changes to the standard data handling and viewing systems of both the analog and digital sections of an organ imaging system since the normal geomtric determination of the position of the scintillations or events will result in both views being obtained simultaneously. This can provide additional information which will enable more accurate background subtraction and blood pool visualization and enable more rapid data collection for the multiple views required in thallium and pyrophosphate studies.

Figure 4:
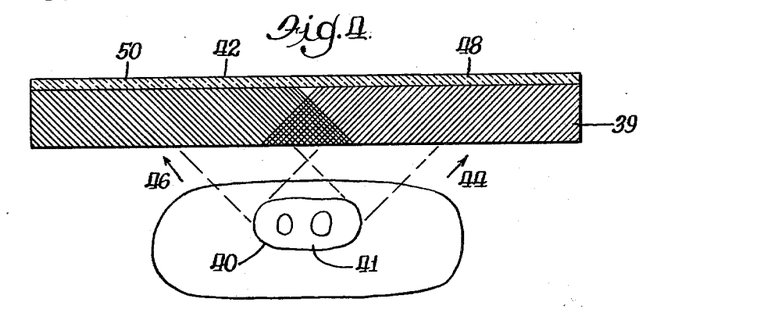
FIG. 4 is a vertical sectional view of the collimator and radiation-detecting material shown imaging a human heart.

With reference to both the first and second embodiments, FIG. 4 is a vertical view of a section 39 having channels 44 and 46, which is a sectional view of collimator 10, imaging a portion 41 of a heart 40 onto a juxtaposed radiation-detecting material 42. Channels 44 and channels 46 of section 39 accept radioactive emissions only in the direction of and coplanar with the axes of channels 44 and 46, respectively. The axes of channels 44 intersect a portion 41 of heart 40 and the axes of channels 46 intersect the same portion 41 of heart 40. Thus both the first plurality of channels 44 and the second plurality of channels 46 are capable of imaging the same portion 41 of heart 40. Radioactive emissions traveling through channels 44 strike on one side 48 of radiation-detecting material 42 thereby producing a first view of portion 41 of heart 40 onto side 48 and radioactive emissions passing through channels 46 strike on the other side 50 of radiation-detecting material 42 thereby producing a second view of portion 41 of heart 40 onto side 50 of radiation-detecting material 42. Thus each section of collimator 10 is associated with two areas of radiation-detecting material 42 which correspond to the two pluralities of channels for each section.

Figure 5:
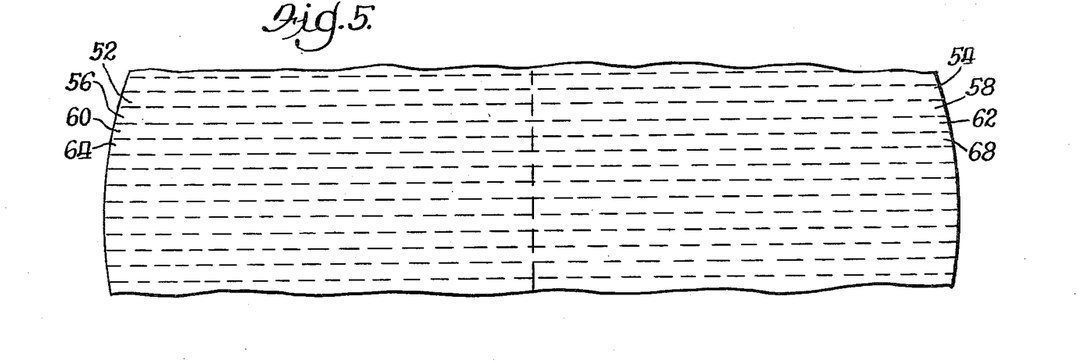
FIG. 5 is a partial bottom view of the radiation-detecting material to facilitate the explanation of the operation of an embodiment of the invention.

Since the sections are parallel and adjacent, the pairs of corresponding areas of radiation-detecting material 42 are substantially parallel and adjacent to each other as shown in FIG. 5. The areas are exaggerated in size for clarity. Thus if areas 52 and 54 of radiation-detecting material 42 correspond with section 14 (FIG. 2), then areas 56 and 58, immediately adjacent to areas 52 and 54 respectively, would correspond with section 15. Similarly, areas 60 and 62 would correspond with section 16 and areas 64 and 68 would correspond with section 17, etc.

Section 14, having a first plurality of channels 70 and a second plurality of channels 72, and section 16, having a first plurality of channels 74 and a second plurality of channels 76, are from the first plurality of sections. Thus channels 70 and 74 both have an angular orientation of 45 degrees and are parallel with each other and channels 72 and 76, having an angular orientation of 135 degrees, are parallel with each other. Channels 70 and 74 therefore produce a composite view comprised of a view of a slice of the organ from an angle of 45 degrees and another view of another slice of the organ also from angle of 45 degrees. Channels 72 and 76 produce a second composite view comprised of two views of the same two respective slices of the organ from an angle of 135 degrees. Thus with a sufficient number of sections, (e.g., at least about 64), the first plurality of sections produces a first and second composite view of the significant parts of the heart organ from an angle of 45 and 135 degrees respectively.

Similarly, section 15, having a first plurality of channels 80 and a second plurality of channels 82, and section 17, having a first plurality of channels 84 and a second plurality of channels 86, are part of the second plurality of sections. Therefore, channels 80 and 84 having an angular orientation of 60 degrees are parallel with each other and channels 82 and 86 having an angular orientation of 120 degrees are parallel with each other. Thus, channels 80 and 84 produce a third composite view of the heart organ from an angle of 60 degrees and channels 82 and 86 produce a fourth composite view from an angle of 120 degrees.

The channels of the collimator may be formed by molding the sections or by some other technique such as sawing or etching the sections. The sections are then stacked and welded or otherwise fastened or bonded together to form the collimator which is assembled into a variety of mountings which can be inserted into a number of different gamma cameras, such as the wide field of view cameras manufactured by Ohio Nuclear, Searle, Union Carbide (Cleon), Picker, and Raytheon. The dimensions of the cross sections of the channels may typically comprise 0.12 inches by 0.12 inches, but of course other dimensions of channels may be employed as a matter of design.

An alternative embodiment may include first and second pluralities of channels of each section that do not intersect although it is generally less advantageous than the preferred embodiment. Since the first and second pluralities of channels have an angular orientation with respect to each other, if the channels do not intersect, a portion of the radiation-detecting material will not correspond with the channels and thus will be wasted.

Area 52 (FIG. 5) of radiation-detecting material 42 corresponds to the first plurality of channels 70 of section 14 and area 60 corresponds to the first plurality of channels 74 of section 16. Therefore, the first composite view is imaged onto areas 52 and 60, respectively. Similarly, the second composite view is imaged onto areas 54 and 62 corresponding to channels 72 and 76, respectively. The third composite view is image onto areas 56 and 64 and the fourth composite view is imaged onto areas 58 and 68. Thus, the areas corresponding to the first composite view alternate with the areas corresponding to the third composite view on one side of radiation-detecting material 42, with the areas corresponding to the second and fourth alternating on the other.

Figure 6:
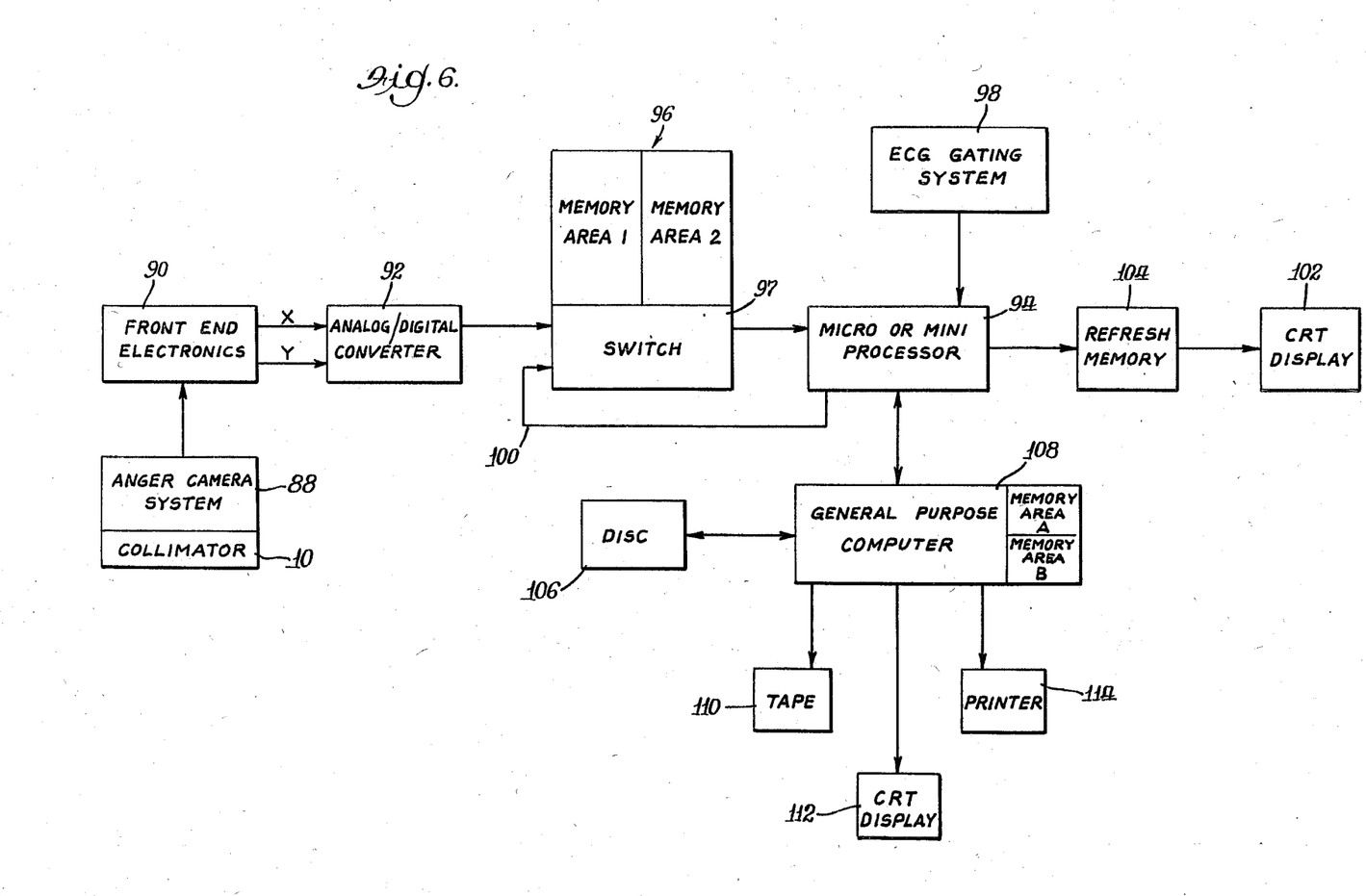
FIG. 6 is a block diagram of an organ imaging system employed in accordance with an embodiment of the invention.

Since the first plurality of sections which produce the first and second composite views alternate with the second plurality of sections which produce the third and fourth composite views, the events of radioactive emissions striking the associated areas of radiation-detecting material 42 must be sorted to assemble the composite views. With reference to FIG. 6, a system is generally shown for imaging organs employing the present invention. Generally, radioactive emissions pass through collimator 10 and strike the radiation-detecting material of a detector means, shown as an Anger-type camera system 88. A locator means, shown as front end electronics 90, assigns planar x,y coordinates to each event of radioactive emission, in a known manner. Analog/digital converter 92 converts the x,y coordinates into digital quantities. Memory 96 is shown in a preferred system to assist the rapid collection of data. Switching the input by a separate controller or by the peripheral processor 94 and switch 97 enables the system to store data and read the data simultaneously, and thus avoid dead time when the data cannot be utilized. In this embodiment, it is desired to display the first and second composite views simultaneously. An electronic sorting means comprising microprocessor or miniprocessor 94 and immediate access memory areas A and B of general computer 108, sorts and stores the events in memory area A if the event corresponds to the first plurality of sections, or stores the event in memory area B if the event corresponds to the second plurality of sections. Alternatively, the general purpose computer 108 or specially designed hardware or firmware could be used. The sorted information is directed to a storage medium which may be part of the peripheral or main computer or a separate memory which may be accessed by either or both computers. An ECG-gating system 98 monitors the beating of the heart and sends this information to processor 94. Processor 94 then stores into memory 96 by means of a data line 100, the time, during each heart beat, in which each event occurs. This information is useful in manipulating the event data to produce more useful information, such as a technique to ensure that the heart beat is divided accurately into the required number of intervals. The views may be displayed in real time by means of a CRT display 102 and memory refresh 104 in order to assure the collimator is correctly aimed and to provide immediate diagnostic information. The data stored in memory areas A and B can be stored in an immediate access memory associated with processor 94 or computer 108 or in an intermediate storage, i.e., disc memory 106, by means of general purpose computer 108 or can be stored in a long term storage, such as tape memory or floppy disc system 110, for example. General purpose computer 108 can manipulate the data into more useful information for diagnostic purposes for display by a CRT display 112 or can print appropriate graphs and statistics by means of a printer 114.

The following algorithm is provided to illustrate a specific method of sorting the events of radioactive emission into their respective composite views of a beating heart. Each beat is divided into a number of equal intervals, 20, for example. Prior to sorting, a count of the total number of events in each interval is produced which is referred to as "number" in the algorithm. Also, a record of the x and y coordinates of each event, the relation to a timing pulse from the computer, and the interval number or marker for each event is recorded. The first and second composite views are stored and displayed together as are the third and fourth composite views. The y coordinate of each event determines which memory area the event is stored in. The events occurring during one interval produce a frame. Each heartbeat is divided into, for example, 20 intervals, therefore, 20 frames are produced for each heartbeat. The total number of heartbeats which are recorded will vary depending on the speed capability of the camera used and the storage capacity and display system used. A time period from, say, 2 to 10 minutes will result in storage of about 150 to 750 beats.

Algorithm 1 frame, beat=0
2 start
3 read next number
4 frame=frame+1
5 if frame=21 then go to L1
6 write frame marker to area A & B
7 N=0
8 L4:N=N+1
9 if N=number+1 go to start
10 read x,y
11 if frac y/2 greater than 0.001 go to L7
12 L6:view=view 3 & 4
13 store view in area B
14 go to L4
15 L7:view=view 1 & 2
16 store in area A
17 go to L4
18 L1:frame=0
19 beat=beat+1
20 if beat=201 then go to end
21 write beat marker
22 go to start
23 end: write end First the frame number, or marker, and beat marker are initialized to zero. Next, the number of events in the particular interval looked at is read in. Then, the frame marker is incremented. Therefore, initially, frame No. 1 is being produced. If 20 frames have already been produced then go to statement L1, otherwise write the frame marker to memory areas A & B. Then, set event processing loop counter N equal to 0. Thus, in statement L4, increment N. If N equals the number of events in the interval, that is, all the events in the interval have been processed, then go back to start, otherwise, read in the coordinates of the next event. If the fractional part of y divided by 2 is greater than 0.001, that is, if the y coordinate is odd, then the event pertains to the first plurality of sections and is part of composite views 1 & 2. The coordinates of that event would then be stored in area A. Otherwise, the y coordinate is even and therefore the event pertains to the second plurality of sections and should be stored in area B. After the coordinates of the event have been stored in the proper memory area, then the process should be repeated for the next event by going back to statement L4. This continues until all the events in the frame have been processed, that is, N=number+1. Then, go back to start. After 20 frames have been produced, then one full beat has been processed and the beat marker should be incremented, stored in memory, and go back to start. If 200 beats have been processed, then go to end.

The complex geometry of the heart makes difficult accurate spatial orientation of events or counts from single views. With the present invention, it is possible to get at least two views of the same organ or portion of the organ simultaneously while the collimator and detector system remain stationary. These views can range from at least 60 degrees left to 60 degrees right of the straight precordial position. Time delays while waiting for a focused camera or a rotating collimator to complete the scan, or delays due to moving the camera are eliminated. This can be very important where critically ill patients are involved. Moreover, the present invention can obtain information that is practically unavailable using collimators of the prior art. This is due to the fact that it is very difficult to produce the second view under the exact conditions that the first view was produced. One difficulty is that a moving organ such as the heart is constantly pumping; therefore it would be difficult to get a second view of the same pumping position as the first view. In addition, the conditions between serial views would be different for studies taken after exercise or pharmacological intervention.

The capacity to determine the three-dimensional orientation of the distribution of radioactive material would enhance the quantitative nature of studies performed with infarct-seeking tracers such as Tc-PYP. Using the present invention with potassium analogs, such as Tl-201, provides a number of two-dimensional views from which a three-dimensional localization of myocardial tissue which excludes the tracer could be constructed to aid diagnosis. The main, immediate gain in pyrophosphate and thallium studies is obtaining the images in one-half or less of the time previously needed, and, secondly, the possibility of obtaining 3D information by further data manipulations.

The following study utilizing four tracer techniques is given as an example of the diagnostic advantages of the invention. First, Thallium 201 myocardial imaging may be undertaken to produce two views of ischemic tissue after the patient has exercised. Since the two views are produced simultaneously, the event (or count) densities measured in each view have exact quantitative relationships, thus eliminating the count difference in the two views due to changes in uptake and washout during the time delay normally encountered with the serial approach necessitated by using conventional collimators. Furthermore, when using conventional collimators, the later views of a Thallium exercise study more closely correspond to a study at rest since the heart has returned to normal rest condition due to the time delay between views. The present invention insures that both views are obtained under identical physiological and hemodynamic conditions with a fixed anatomical and geometric relationship between views.

Following the Thallium study, a study may be undertaken using $Tc^{99m}$ labelled pyrophosphate for acute infarcted tissue imaging. Then, $Tc^{99m}$ human serum albumin can be bolus injected for a first pass hemodynamic study to produce another set of two views. In systems incapable of first pass studies multiple-gated studies can be used. The hemodynamics are in exact time correlation in both views taken since they are obtained exactly at the same time from the same blood corpuscles in both views. Thus, if one view is an End Diastole anterior view, then a left anterior oblique view could be obtained at End Diastole under the exact same conditions. This holds true for all intervals of a representative cardiac cycle.

An ECG-gated blood pool imaging study may then follow the first pass study. Multiple ECG-gated views are obtained simultaneously so that each discrete phase of the cardiac cycle is exactly synchronous in each pair of views obtained. Analysis of left ventricle hemodynamics from the left view would be improved by added data from the right views. Useful data to aid background subtraction and accurate delineation of the heart septa and chambers would be available.

These and other studies can all be done serially without once moving the camera or the patient. This assures exact anatomic and geometric registration of all studies for both views for the entire series. This capability can aid in infarct sizing from the pyrophosphate study. Furthermore, it allows precise overlays of regions of acute infarct with regions of ischemia, regions of old infarct or scar determined by the Thallium study, and regions of akinetic wall segments from the first pass and multiple-gated studies.

Alternative uses of the invention include techniques for rotating the collimator of the present invention to provide further additional views. Additionally, the collimator of the present invention may be used to provide multiple images for stereoscopic three-dimensional viewing of an organ.

It will, of course, be understood that modification of the present invention in its various aspects will be apparent to those skilled in the art, some being apparent only after study and others being a matter of routine design. As such, the scope of the invention should not be limited by the particular embodiment and specific construction herein described, but should be defined only by the appended claims and equivalents thereof.

Various features of the invention are set forth in the following claims.

What is claimed is:

1. A collimator for use in imaging a portion of a body with a camera having a radiation detecting surface, the collimator having mounting means for attachment to said camera adjacent to said radiation detecting surface, and comprising a body of substantially radiation-impervious material defining two or more groups of channels, each group comprising a plurality of channels having axes intersecting a portion of the body being viewed on one side of the collimator and intersecting the radiation detecting surface of the camera on the other side of the collimator, and simultaneously producing a number of different views of said body corresponding respectively to the number of said groups of channels, each axis of each channel lying in a plane approximately perpendicular to the plane of the radiation-detecting surface and all of such planes containing said axes being approximately parallel to each other throughout all of the groups of channels of the collimator when said collimator is mounted to the camera.

2. The collimator of claim 1 wherein the axes of the channels of each group of channels are substantially in parallel with each other within each respective group.

3. The collimator of claim 1 wherein a portion of groups of channels intersect.

4. The collimator of claim 1 wherein the collimator is capable of rotation so that additional views can be produced by the collimator.

5. The collimator of claim 1 in combination with a radiation-detecting material juxtaposed with the collimator; a detector means coupled with the radiation-detecting material to detect an event of radiation impinging on the radiation-detecting material; and means operatively connected to the detector means for displaying the views.

6. The collimator of claim 1 wherein said body of substantially radiation-impervious material comprises a plurality of substantially parallel adjacent sections of said substantially radiation-impervious material, each of said sections defining a portion of one or more groups of channels.

7. The collimator of claim 6 wherein each of said plurality of parallel, adjacent sections of substantially radiation-impervious material has a base and a plurality of septa carried by the base, said base and plurality of septa defining said portion of groups of channels.

8. The collimator of claim 6 wherein said body of substantially radiation-impervious material further comprises a second plurality of substantially parallel adjacent sections, each of the second plurality of sections defining a portion of one or more groups of channels.

9. The collimator of claim 8 wherein said first and second pluralities of sections are intermixed so that a number of different composite views are produced corresponding respectively to the number of said groups of channels of said first and second pluralities of sections.

10. The collimator of claim 9 wherein said first and second pluralities of sections alternate.

11. The collimator of claim 8 in combination with a radiation-detecting camera coupled to the collimator for providing data signals in response to radiation from the collimator, data processing means operatively connected to the camera for sorting said data signals according to the view to which the data pertains and a first display means operatively connected to the data processing means for displaying images of the portions of the body corresponding to said views in real time.

12. The combination of claim 11 wherein the data processing means includes a memory having a first and second area for storing the data pertaining to the first and second pluralities of sections, respectively.

13. The combination of claim 11 wherein the combination further comprises a gating system responsive to signals derived from an organ having a cyclic motion and operatively connected to the processing means to provide timing information signals to enable the data processing means to determine the portion of the cycle to which the data from the camera pertains.

14. The combination of claim 11 wherein the data processing means includes a disc memory for storing the data from the camera.

15. The combination of claim 11 wherein the data processing means includes a tape memory for storing the data.

16. The combination of claim 11 wherein the data processing means comprises a first data processor for sorting said data signals according to the view to which the data pertains and a second data processor for further processing said data to obtain medical diagnostic information.

17. The combination of claim 16 wherein the combination further comprises a second display means operatively connected to the second data processor for displaying images of the portion of the body from said further processed data.

18. The combination of claim 16 wherein the combination further comprises a printer operatively connected to the second data processor for printing said medical diagnostic information.

19. The collimator for use in imaging a portion of a body with a radiation-detecting camera, comprising a body of substantially radiation-impervious material defining a first plurality of channels, said first plurality of channels each having an axis, said axes of the first plurality of channels intersecting at least a portion of the body, thereby producing a first view of a portion of the body; and said body of substantially radiation-impervious material also defining a second plurality of channels, a portion of said second plurality of channels intersecting a portion of said first plurality of channels, said second plurality of channels each having an axis, said axes of the second plurality of channels at least partially intersecting the same portion of the body as the axes of the first plurality of channels, thereby simultaneously producing a second view of the same portion of the body.

20. The collimator of claim 19 wherein said axes of the first plurality of channels are substantially in parallel with each other and said axes of the second plurality of channels are substantially in parallel with each other.

21. The collimator of claim 19 wherein substantially all of the first plurality of channels and substantially all of the second plurality of channels intersect.

22. The collimator of claim 19 wherein the collimator is capable of rotation so that additional views can be produced by the collimator.

23. The collimator of claim 19 in combination with a radiation-detecting material juxtaposed with the collimator; a detector means coupled with the radiation-detecting material to detect an event of radiation impinging on the radiation-detecting material; and means operatively connected to the detector means for displaying the views.

24. The collimator of claim 19 wherein said body of substantially radiation-impervious material comprises a plurality of substantially parallel adjacent sections of said substantially radiation-impervious material, each of said sections defining a portion of said first and second pluralities of channels.

25. The collimator of claim 24 wherein each of said plurality of parallel, adjacent sections of substantially radiation-impervious material has a base and a plurality of septa carried by the base, said base and plurality of septa defining said portion of said first and second pluralities of channels.

26. The collimator of claim 24 wherein said body of substantially radiation-impervious material further comprises a second plurality of substantially parallel adjacent sections defining a third and fourth plurality of channels, said third plurality of channels each having an axis intersecting a portion of the body thereby producing a third view of the portion of the body, said fourth plurality of channels each having an axis intersection the same portion of the body as the axes of the third plurality of channels thereby producing a fourth view of the same portion of the body.

27. The collimator of claim 26 wherein said first and second pluralities of sections are intermixed so that said first plurality of channels of said first plurality of sections produces a first composite view, said second plurality of channels of said first plurality of sections produces a second composite view, said third plurality of channels of said second plurality of sections produces a third composite view, and said fourth plurality of channels of said second plurality of sections produces a fourth composite view.

28. The collimator of claim 27 wherein said first and second pluralities of sections alternate.

29. The collimator of claim 26 in combination with a radiation-detecting camera coupled to the collimator for providing data signals in response to radiation from the collimator, data processing means operatively connected to the camera for sorting said data signals according to the view to which the data pertains and a first display means operatively connected to the data processing means for displaying images of the portions of the body corresponding to said views in real time.

30. The combination of claim 29 wherein the data processing means includes a memory having a first and second area for storing the data pertaining to the first and second pluralities of sections, respectively.

31. The combination of claim 29 wherein the combination further comprises a gating system responsive to signals derived from an organ having a cyclic motion and operatively connected to the processing means to provide timing information signals to enable the data processing means to determine the portion of the cycle to which the data from the camera pertains.

32. The combination of claim 29 wherein the data processing means includes a disc memory for storing the data from the camera.

33. The combination of claim 29 wherein the data processing means includes a tape memory for storing the data.

34. The combination of claim 29 wherein the data processing means comprises a first data processor for sorting said data signals according to the view to which the data pertains and a second data processor for further processing said data to obtain medical diagnostic information.

35. The combination of claim 34 wherein the combination further comprises a second display means operatively connected to the second data processor for displaying images of the portion of the body from said further processed data.

36. The combination of claim 34 wherein the combination further comprises a printer operatively connected to the second data processor for printing said medical diagnostic information.

37. A collimator for use in imaging a portion of a body with a radiation-detecting camera, comprising a body of substantially radiation-impervious material defining a first plurality of channels, said first plurality of channels each having an axis, said axes of the first plurality of channels being substantially in parallel with each other and intersecting at least a portion of the body, thereby producing a first view of a portion of the body; and said body of substantially radiation-impervious material also defining a second plurality of channels, a portion of said second plurality of channels intersecting at least a portion of said first plurality of channels, said second plurality of channels each having an axis, said axes of the second plurality of channels being substantially in parallel with each other and at least partially intersecting the same portion of the body as the axes of the first plurality of channels, thereby simultaneously producing a second view of the same portion of the body.

38. The collimator of claim 37 wherein substantially all of the first plurality of channels and substantially all of the second plurality of channels intersect.

39. A collimator for use in imaging a portion of a body with a radiation-detecting camera, comprising a disk, said disk comprising a plurality of stacked parallel adjacent sections of substantially radiation-impervious material, each of said sections defining a first and second plurality of channels, each of said channels having an axis, the axes of the first plurality of channels being in parallel with each other and with the axes of the other first pluralities of channels and intersecting at least a portion of the body, thereby producing a first view of the portion of the body, and the axes of the second plurality of channels being in parallel with each other and with the axes of the other second pluralities of channels and intersecting the same portion of the body as the axes of the first pluralities of channels, thereby simultaneously producing a second view of the same portion of the body.

40. A collimator for use in imaging a portion of the body with a radiation-detecting camera, comprising a plurality of parallel, adjacent sections of stacked substantially radiation-impervious material, each of said sections having a base and a plurality of septa carried on the base, said base and plurality of septa defining a first plurality of channels each having an axis, said axes of the first plurality of channels being substantially in parallel with each other and with the axes of the other first pluralities of channels and intersecting a portion of the body thereby producing a first view of the portion of the body, and said base and plurality of septa also defining a second plurality of channels each having an axis, said axes of the second plurality of channels being substantially in parallel with each other and with the axes of the other second pluralities of channels and intersecting the same portion of the body as the axes of the first plurality of channels, thereby producing a second view of same portion of the body so that said plurality of sections produce a first view of a portion of the body comprised of the plurality of first views of portions of the body produced by the plurality of sections and also produce a second view of the same portion of the body as the first plurality of channels, comprised of the plurality of second views of portions of the body produced by the plurality of sections.

41. The collimator of claim 40 wherein a portion of the first plurality of channels and a portion of the second plurality of channels of each section intersect.

42. A collimator for use in imaging a portion of a body with a radiation-detecting camera, comprising at least four adjacent sections wherein each of said sections views a separate portion of the body; each of said sections comprising a body of substantially radiation-impervious material defining a first plurality of channels, said first plurality of channels each having an axis, said axes of the first plurality of channels being substantially in parallel with each other and intersecting a portion of the body, thereby producing a first view of the portion of the body, and said body of substantially radiation-impervious material also defining a second plurality of channels, said second plurality of channels each having an axis, said axes of the second plurality of channels being substantially in parallel with each other and intersecting the same portion of the body as the axes of the first plurality of channels, thereby producing a second view of the same portion of the body, so that a first section of the collimator produces a first and second view of a first portion of the body, a second section produces a first and second view of a second portion of the body, a third section produces a first and second view of a third portion of the body and a fourth section produces a first and second view of a fourth portion of the body; the axes of the first plurality of channels of the first and third sections being substantially in parallel with each other thereby producing a first composite view, the first composite view being a view of the first and third portions of the body and being comprised of the first views produced by the first and third sections, the axes of the second plurality of channels of the first and third sections being substantially in parallel with each other thereby producing a second composite view, the second composite view being a second view of the first and third portions of the body and being comprised of the second views produced by the first and third sections, the axes of the first plurality of channels of the second and fourth sections being substantially in parallel with each other, thereby producing a third composite view, the third composite view being a view of the second and fourth portions of the body and being comprised of the first views produced by the second and fourth sections, and the axes of the second plurality of channels of the second and fourth sections being substantially in parallel with each other, thereby producing a fourth composite view, the fourth composite view being a second view of the second and fourth portions of the body and being comprised of the second views produced by the second and fourth sections.

43. The collimator of claim 42 wherein a portion of the first plurality of channels and a portion of the second plurality of channels intersect.

44. The collimator of claim 42 wherein substantially all of the first plurality of channels and substantially all of the second plurality of channels intersect.

45. A system for imaging a portion of a body including: a collimator comprising a body of substantially radiation-impervious material defining a first plurality of channels, said first plurality of channels each having an axis, said axes of the first plurality of channels intersecting at least a portion of the body, thereby producing a first view of the portion of the body and said body of substantially radiation-impervious material also defining a second plurality of channels, said second plurality of channels each having an axis, said axes of the second plurality of channels at least partially intersecting the same portion of the body as the axes of the first plurality of channels, thereby simultaneously producing a second view of the same portion of the body; a radiation-detecting material juxtaposed with the collimator; a detector means coupled with the radiation-detecting material to detect an event of radiation impinging on the radiation-detecting material; and means operatively connected to the detector means for displaying the views; said collimator being rotatable so that additional views can be produced by the collimator.

46. A system for imaging a portion of a body including; a collimator comprising a body of substantially radiation-impervious material defining a first plurality of channels, said first plurality of channels each having an axis, said axes of the first plurality of channels being substantially in parallel with each other and intersecting at least a portion of the body, thereby producing a first view of the portion of the body and said body of substantially radiation-impervious material also defining a second plurality of channels, said second plurality of channels each having an axis, said axes of the second plurality of channels being substantially in parallel with each other and at least partially intersecting the same portion of the body as the axes of the first plurality of channels, thereby simultaneously producing a second view of the same portion of the body; a radiation-detecting material juxtaposed with the collimator; a detector means coupled with the radiation-detecting material to detect an event of radiation impinging on the radiation-detecting material; and means operatively connected to the detector means for displaying the views; said collimator being rotatable so that additional views can be produced by the collimator.

47. A system for imaging a body including: a collimator comprising at least four adjacent sections wherein each of said sections views a separate portion of the organ; each of said sections comprising a body of substantially radiation-impervious material defining a first plurality of channels, said first plurality of channels each having an axis, said axes of the first plurality of channels being substantially in parallel with each other and intersecting a portion of the body, thereby producing a first view of the portion of the body, and said body of substantially radiation-impervious material also defining a second plurality of channels, said second plurality of channels each having an axis, said axes of the second plurality of channels being substantially in parallel with each other and intersecting the same portion of the body as the axes of the first plurality of channels, thereby producing a second view of the same portion of the body, so that a first section of the collimator produces a first and second view of a first portion of the body, a second section produces a first and second view of a second portion of the body, a third section produces a first and second view of a third portion of the body and a fourth section produces a first and second view of a fourth portion of the body; the axes of the first plurality of channels of the first and third sections being substantially in parallel with each other thereby producing a first composite view, the first composite view being a view of the first and third portions of the body and being comprised of the first views produced by the first and third sections, the axes of the second plurality of channels of the first and third sections being substantially in parallel with each other thereby producing a second composite view, the second composite view being a second view of the first and third portions of the body and being comprised of the second views produced by the first and third sections, the axes of the first plurality of channels of the second and fourth sections being substantially in parallel with each other, thereby producing a third composite view, the third composite view being a view of the second and fourth portions of the body and being comprised of the first views produced by the second and fourth sections, and the axes of the second plurality of channels of the second and fourth sections being substantially in parallel with each other, thereby producing a fourth composite view, the fourth composite view being a second view of the second and fourth portions of the body and being comprised of the second views produced by the second and fourth sections; a radiation-detecting material juxtaposed with the collimator; a detector means coupled with the radiation-detecting material to detect an event of radiation striking the radiation-detecting material; locator means operatively connected to the detector means for assigning coordinates to each event; sorting means, operatively connected to the locator means, including a memory having at least two areas, said sorting means for sorting the events as to the composite view the event corresponds based on the coordinates assigned to each event by the locator means; and display means operatively connected to the memory for selectively displaying the composite views.

48. A system for imaging a portion of a body including: a collimator comprising a body of substantially radiation-impervious material defining a first plurality of channels, said first plurality of channels each having an axis, said axes of the first plurality of channels being substantially in parallel with each other and intersecting a portion of the body, thereby producing a first view of the portion of the body; and said body of substantially radiation-impervious material also defining a second plurality of channels, a portion of said second plurality of channels intersecting at least a portion of said first plurality of channels, said second plurality of channels each having an axis, said axes of the second plurality of channels being substantially in parallel with each other and intersecting the same portion of the body as the axes of the first plurality of channels, thereby simultaneously producing a second view of the same portion of the body; a radiation-detecting camera coupled to the collimator for providing data signals in response to radiation from the collimator; data processing means operatively connected to the camera for sorting said data signals according to the view to which the data pertains and a first display means operatively connected to the data processing means for displaying images of the portions of the body corresponding to said views in real time.

49. The system of claim 48 wherein the data processing means includes a memory having a first and second area for storing the data pertaining to the first and second views respectively.

50. The system of claim 48 wherein the system further comprises a gating system responsive to signals derived from an organ having a cyclic motion and operatively connected to the processing means to provide timing information signals to enable the data processing means to determine the portion of the cycle to which the data from the camera pertains.

51. The system of claim 48 wherein the data processing means includes a disc memory for storing the data from the camera.

52. The system of claim 48 wherein the data processing means includes a tape memory for storing the data.

53. The system of claim 48 wherein the data processing means comprises a first data processor for sorting said data signals according to the view to which the data pertains and a second data processor for further processing said data to obtain medical diagnostic information.

54. The system of claim 53 wherein the system further comprises a second display means operatively connected to the second data processor for displaying images of the portion of the body from said further processed data.

55. The system of claim 53 wherein the system further comprises a printer operatively connected to the second data processor for printing said medical diagnostic information.

* * * * *